United States Patent [19]

Castillo et al.

[11] Patent Number: 5,091,185
[45] Date of Patent: Feb. 25, 1992

[54] COATED VETERINARY IMPLANTS

[75] Inventors: Ernesto J. Castillo, St. Peters; Kenneth E. Eigenberg, St. Louis; Kanaiyalal R. Patel, Creve; Milton J. Sabacky, Ballwin, all of Mo.

[73] Assignee: Monsanto Company, St. Louis, Mo.

[21] Appl. No.: 541,114

[22] Filed: Jun. 20, 1990

[51] Int. Cl.⁵ .................................. A23K 1/18
[52] U.S. Cl. ........................ 424/438; 424/423; 424/424; 424/425; 424/426; 424/476
[58] Field of Search ............... 424/423, 424, 425, 426, 424/476, 438

[56] References Cited

U.S. PATENT DOCUMENTS

| | | | |
|---|---|---|---|
| 4,173,626 | 11/1979 | Dempski et al. | 424/19 |
| 4,526,938 | 7/1985 | Churchill et al. | 525/415 |
| 4,738,679 | 4/1988 | Seamark et al. | 604/892 |
| 4,761,289 | 8/1988 | Shalati et al. | 424/468 |
| 4,765,980 | 8/1988 | DePrince | 424/108 |
| 4,786,501 | 11/1988 | Janski et al. | 424/422 |
| 4,793,997 | 12/1988 | Drake | 424/426 |
| 4,808,353 | 2/1989 | Nambu et al. | 264/28 |
| 4,837,033 | 6/1989 | Kokubo et al. | 424/494 |
| 4,863,736 | 9/1989 | Azain et al. | 424/423 |
| 4,882,137 | 11/1989 | Staples et al. | 424/423 |
| 4,882,167 | 11/1989 | Jang | 424/468 |
| 4,891,223 | 1/1990 | Ambegaonkar et al. | 424/408 |

FOREIGN PATENT DOCUMENTS

87/06828 11/1987 Australia .

OTHER PUBLICATIONS

Kirk-Othmer, "Encyclopedia of Chemical Technology", vol. 23 (3rd Ed), pp. 848–865.

Primary Examiner—Thurman K. Page
Assistant Examiner—D. Gabrielle Phelan
Attorney, Agent, or Firm—Wayne R. Eberhardt

[57] ABSTRACT

Solid dosage forms of bioactive materials for parenteral administration such as porcine or bovine somatotropin pellets intended for subcutaneous implantation to improve food production of farm animals are coated with polyvinyl alcohol to extend the release characteristics of the material. The polyvinyl alcohol preferably has a molecular weight of from about 20,000 to 100,000, a degree of hydrolysis of at least about 98%, and is applied from an aqueous solution by spray coating to form a continuous uniform covering 3 to 25 μm PVA/mm².

10 Claims, No Drawings

COATED VETERINARY IMPLANTS

FIELD OF INVENTION

This invention relates to veterinary implants comprising bioactive materials and, more particularly, to implantable somatotropin pellets enveloped with a polymeric coating to prolong the release of the somatotropin upon implantation.

BACKGROUND

Bioactive materials including drugs, hormones and the like are administered to animals by injection of liquid formulations or implantation of solid compositions. While injections may be made on a daily basis, sustained release formulations are usually preferred for parenteral administration of bioactive materials to moderate the release of the active agent, to reduce initial spiking of concentrations in the body, and to reduce the frequency with which the material must be administered. This is particularly true in the case of hormones which are preferably administered to animals at a relatively constant rate over a period of several weeks or months.

Somatotropin, a growth hormone which can be produced reliably and inexpensively in large quantities by recombinant DNA technology, is known to be effective in increasing milk production of dairy cattle and in improving meat production of beef cattle and swine. Somatotropin formulations having prolonged release characteristics have been prepared by dispersing somatotropin in a vegetable oil carrier for injection as described for example in EP 177,478. Aqueous formulations of somatotropin intended for administration over an extended period by means of an implanted osmotic pump delivery device are described in U.S. Pat. No. 4,855,141.

Solid pellets of somatotropin adapted for parenteral administration by implantation and having at least one uncoated release surface are described in U.S. Pat. No. 4,863,736, incorporated herein by reference. According to this patent, solid pellets of somatotropin produced by recombinant DNA technology and which are essentially free of binder or matrix polymers are formed by dry compression. The pellets may be partially coated with a barrier type polymer to substantially inhibit release of the somatotropin from the coated surfaces. Examples of suitable materials that can be used to provide the partial coating for the somatotropin pellet are disclosed to include shellac, bees wax, cellulose acetate butyrate, polylactic acid, ethyl cellulose, silicones, ethylene vinyl acetate co-polymer, hydroxy propyl cellulose, polycarbonate, polycaprolactone cellulose acetate, polymethyl methacrylate and other polymers known for use as barrier coatings.

As further disclosed in this U.S. patent, at least one surface of the pellet is left uncoated to provide a primary release surface for the somatotropin. In the case where the pellet is formed in a cylindrical shape, it is generally preferred to coat the cylindrical surface while leaving one or both ends of the cylinder uncoated. The rate of release of somatotropin from a pellet partially coated with a barrier type polymer increases with the surface area of the uncoated portion.

As further disclosed in this reference at column 9, lines 32-63, the coated pellets may additionally be provided with a "temporary protective covering" i.e., a light polymeric covering "to protect the article during storage and handling, and possibly to be of assistance in the administration of the article to the animal." Such temporary protective coverings are either removed prior to implantation of the pellet or are quickly removed from the pellet by surrounding tissue fluids after implantation. In either case, the temporary protective covering is disclosed to have little or no effect on somatotropin release rates, and is thereby distinguished from the "coating" utilized for the purpose of providing prolonged release delivery as described in the reference. Suitable materials useful as such temporary protective coverings which dissolve and/or melt after implantation are reported to include polyvinyl alcohol, sugars and polyethylene glycol such as PEG 8000.

It is an object of the present invention to provide a new delivery system for the parenteral administration of somatotropin and other biologically active materials to animals. It is a further object of this invention to provide a solid pellet of somatotropin or other biologically active material having sustained release delivery characteristics. It is a yet further object of this invention to provide a coating for solid pellets of somatotropin and other biologically active materials which may be uniformly applied to all surfaces of the pellet to impart sustained release properties upon implantation. It is a yet further object of this invention to provide a solid pellet of somatotropin or other biologically active material which is totally eveloped by a polymeric coating which imparts prolonged release characteristics to the pellet through parenteral administration. These and other objects of this invention will be apparent from the ensuing description and Examples.

SUMMARY

The present invention provides for the sustained release of somatotropin and other biologically active materials through parenteral administration by implantation of solid pellets of the active material coated with a composition comprising polyvinyl alcohol (PVA). The polymer is preferably applied to all surfaces of the pellet by spray coating or other suitable means to form a continuous, uniform covering. The polyvinyl alcohol preferably has a molecular weight of at least about 10,000 and a degree of hydrolysis greater than about 95%, and is applied to the pellet from an aqueous solution comprising from about 2 to 10% by weight polymer. When applied to the pellet at a level of about 0.5 to 5% by weight, the polymeric coating effectively controls the release of the active material after implantation to provide a more uniform rate of delivery over a longer period of time as compared to uncoated pellets. The coating process is economical and readily accomplished using pellet coating techniques conventional in the pharmaceutical industry.

DETAILED DESCRIPTION OF INVENTION

As used herein, the following terms have the meanings set forth below.

"Parenteral administration" means the administration of a bioactive material directly to an animal by injection, implantation or insertion into a body cavity as opposed to topical or oral administration. Parenteral administration by implantation of solid compositions may be intramuscular or subcutaneous and may be accomplished surgically or by injecting small pellets through a needle using an instrument designed for that purpose. In the case of the present invention, subcutaneous injection of coated pellets is the preferred method of administration.

"Quick release" means a dosage form which releases the bulk of its active agent rapidly upon parenteral administration, characterized by a rapid rise in serum concentration to a peak value followed by a steady decrease approaching zero. Administration of quick release compositions is generally on a daily schedule if an extended period of treatment is required.

"Sustained release" or "prolonged release" means a dosage form which releases gradually upon parenteral administration as indicated by a steady and prolonged effect over a specific period of days or weeks until the active agent is substantially extracted from the composition. An initial peak in serum concentration may be seen in some sustained release formulations.

"Growth hormones" are naturally occurring proteins or variants thereof which demonstrates specific hormonal activity. The term includes complete hormones and bioactive fragments of such hormones which may, for example, have varying portions of the amino terminal ends of the hormone deleted, and bioactive analogs of such hormones with one or more substitutions and/or modifications in the protein sequence which does not destroy the biological activity of the protein.

"Bovine growth hormone" or bGH is understood to refer to any protein having bovine growth hormone activity, while "porcine growth hormone" or pGH is similarly understood to refer to any protein having porcine growth hormone activity. BGH and pGH polypeptides lacking various portions of the amino terminal end of the natural hormones have been shown to retain their biological activity.

"Somatotropin" means any polypeptide that has biological activity and chemical structure similar to that of a somatotropin produced in the pituitary gland of an animal. Such somatotropins include natural somatotropin produced by pituitary somatotropic cells and, alternatively, somatotropin produced by recombinant DNA technology in which somatotropin is expressed by genetically transformed bacterial cells. Such recombinant DNA produced somatotropin may have an amino acid sequence identical to a naturally occurring somatotropin, or may comprise variants in which amino acid residues are either added to, subtracted from or different than the amino acid sequence of the naturally occurring material, provided that such additions, deletions or changes in the amino acid sequence do not destroy the bioactivity of the somatotropin. Also included are the somatotropins which are associated with anions or cations, particularly salts, complexes or combinations with metal ions. Examples of suitable monovalent metal ions include sodium and potassium while examples of suitable polyvalent metal ions include zinc, iron, calcium, bismuth, barium, magnesium, manganese, aluminum, copper, cobalt, nickel and cadmium. Suitable anions include bicarbonate, acetate, glycine and borate.

Examples of somatotropins useful in the current invention include avian somatotropin for treating chickens, turkeys and the like, mammalian somatotropin for treating cattle, swine, sheep, goats and the like, and aquatic somatotropin for treating fish and the like. Particularly useful are the bovine and porcine somatotropins which are known to be effective in increasing food production of farm animals. Specific bovine and porcine somatotropins prepared by recombinant DNA technology and metal complexes thereof as specifically described in U.S. Pat. No. 4,863,736, supra, include the following:

MBS—methionyl-bovine somatotropin
ABS—ala-val-bovine somatotropin
APS—alanyl-porcine somatotropin
MPS—methionyl-porcine somatotropin
ZnMBS—zinc associated MBS
CuAPS—copper associated APS The somatotropin may be pelletized by dry compression using standard tabletting techniques. If desired, binders, lubricants, fillers and the like may be incorporated to facilitate the tabletting process while bacteriostats, antioxidants, anti-inflammatory agents, antibiotics and the like may be incorporated for therapeutic effect.

Somatotropin pellets may be produced in conventional tabletting machines utilizing dies of appropriate size and shape and at pressures within conventional ranges. Conventional handling and tabletting procedures can be followed. For instance, the somatotropin can be precompacted and comminuted to improve handling characteristics and flowability. The tablets are preferably cylindrical in shape although spherical, oval or other shapes may be used. Cylindrical pellets having a diameter from about 0.5 to 3.5 mm and a length of from about 1 to 3 times the diameter are particularly preferred since this size and shape permits implantation by injection through an appropriately sized needle. Such pellets may be injected singly or in stacked arrays of two to ten or more if higher dosage forms are desired.

The polyvinyl alcohol coating may be applied to the pellets using any of the conventional coating methods commonly employed in the pharmaceutical industry for coating medical tablets. One such method is the air suspension or fluidized bed process wherein the pellets are suspended in a cylindrical chamber by an upward moving stream of air. The coating solution is atomized and sprayed onto the suspended particles which are maintained in the suspended state until the coating dries. The constant movement of the pellets assures uniform application of the coating. The spray application and drying time of the process are dependent upon the concentration of polymer in solution, the atomization rate, the temperature and flow rate of the supporting air stream, and the desired weight or thickness of coating.

Disadvantages of the fluidized bed coating process include a significant degree of tablet abrasion and coating material loss, as well as the large volumes of fluidizing air which require high energy use and the need for pollution control equipment of large capacity. An alternative method of coating tablets commonly used in the pharmaceutical industry is the pan coating process in which tablets are sprayed with a solution of the coating material while being gently tumbled in a rotating drum equipped with internal baffles. The drum may be perforated to permit drying air to flow through the pellets during application of the coating solution. This method has the advantage of using compact equipment with low energy requirements and high efficiency, although drying efficiency is less than that of the fluidized bed method. The coating is preferably applied from an aqueous based solution to minimize vapor disposal problems.

The polyvinyl alcohol coating may be applied to the somatotropin pellets according to the present invention from an aqueous solution containing from about 2 to about 10% polymer. The coating may comprise from about 0.5 to 5% by weight of the coated tablet, preferably 1 to 3%, and is preferably present as a continuous, uniform covering having a weight of from about 3 to 25 ug/mm$^2$, and most preferably from about 5 to 15 ug/mm$^2$. The PVA polymer preferably has a nominal molecular weight (based on viscosity) of from about 10,000 to 150,000 or higher, most preferably from about 20,000 to 100,000, and a degree of hydrolysis greater than about 95% and most preferably greater than 98%.

The physical properties of PVA are primarily dependent upon molecular weight and degree of hydrolysis. Commercial products are generally classified into four nominal molecular weight (Mn) ranges according to viscosity grade, and three degrees of hydrolysis according to mole percent residual acetate groups in the resin, as follows (Source: Kirk-Othmer "Encyclopedia of Chemical Technology," Third Edition, Vol. 23, pp 848-865):

| Viscosity Grade | Mn | 4% soln. viscosity* |
|---|---|---|
| low | 25,000 | 5-7 |
| intermediate | 40,000 | 13-16 |
| medium | 60,000 | 28-32 |
| high | 100,000 | 55-65 |

*Brookfield mPa.s at 20° C.

| Residual Acetate Groups, mol % | Degree of Hydrolysis |
|---|---|
| 1-2 | fully hydrolyzed (98+%) |
| 3-9 | intermediate |
| 10-15 | partially hydrolyzed |

The water sensitivity of PVA, or the rate at which it goes into solution, is controlled primarily by the degree of hydrolysis. Fully hydrolyzed polymers have a high degree of water resistance, and dissolve very slowly at temperatures below about 60° C. For purposes of the present invention, a low level of water sensitivity is desired and fully hydrolyzed polymers are preferred. Water sensitivity of PVA is also influenced to a lesser degree by molecular weight, with higher molecular weight polymers having increased water resistance.

The following examples are provided to illustrate the present invention and are not intended as limiting. All parts and percentages are by weight unless otherwise specified.

EXAMPLE 1

Compacted pellets were prepared from copper associated porcine somatotropin (CuAPS) produced as described in U.S. Pat. No. 4,863,736 and having a 2:1 Cu:APS molar ratio. The pellets were prepared with diameters of 2.4, 2.8 and 3.2 mm and in weights ranging from 10 to 56 mg. The pellets were spray coated in a fluidized bed with approximately 2.5% by weight PVA using a 10% aqueous solution of Elvanol TM PVA, a fully hydrolyzed polymer having a nominal molecular weight Mn of 50,000 available from E. I. DuPont de Nemours, Wilmington, Del. The biological activity of the coated pellets was determined in a rat assay which measures the weight gain response resulting from the treatment and has been shown to be a good predictor of activity in swine. In the rat test, groups of ten Sprague-Dawley female rats weighing 200-225 g are surgically implanted with sufficient pellets to provide the target dose by placing the pellets subcutaneously through a lateral incision in the back of the animal. Rats implanted with uncoated pellets are included as a control to demonstrate the effect of the coating, and untreated rats are included to establish baseline performance.

The rats are housed individually, provided with food and water ad libitum, and exposed to a 12 hour light-/dark cycle. The animals are weighed daily over a test period of about 25 days, and the average cumulative weight gain of each test group is plotted to show the performance of the group. The difference in rate and degree of average weight gain between rats implanted with pellets and the untreated animals is taken as an indication of the biological response to the pellets. Peak weight gain, i.e., the maximum weight gain advantage of the treated animals in each test group over the untreated animals, and the day of the test on which this peak weight gain is realized, are the two primary indicators showing the extent and duration of the biological response for the test group.

In this Example, the target dose of CuAPS was 100 mg, and sufficient pellets of each size and weight were implanted to provide actual dose levels from 80 to 112 mg depending on the available pellet weights (e.g. 10×10 mg, 2×40 mg, 2×56 mg, 3×30 mg, 5×20 mg, etc.)

A second series of CuAPS pellets having weights from 10 mg to 56 mg and diameters of 2.4, 2.8 and 3.2 mm were spray coated to provide a uniform average coating of about 11 ug/mm$^2$ of pellet surface area.

The results obtained by rat assay in the above studies are illustrated by the data presented in Tables I and II below.

TABLE I

Peak Weight Gain
CuAPS Pellets Coated With 2.5% by wt. PVA

| Diameter/wt | 10 mg | 12 mg | 20 mg | 30 mg | 40 mg | 50 mg | 56 mg |
|---|---|---|---|---|---|---|---|
| 2.4 mm | 78 g | 53 g | 65 g | 57 g | — | — | — |
| (ug/mm$^2$)* | (10.7) | (11.3) | (13.5) | (14.0) | | | |
| 2.8 mm | 81 g | — | 67 g | 53 g | — | — | — |
| (ug/mm$^2$) | (11.0) | | (14.0) | (14.7) | | | |
| 3.2 mm | — | — | 74 g | 61 g | 53 g | 48 g | 54 g |
| (ug/mm$^2$) | | | (13.4) | (15.4) | (15.5) | (16.3) | (17.6) |

Uncoated Controls - 58 g (Avg)
*Calculated coating coverage at 2.5% by weight PVA

TABLE II

Peak Weight Gain
CuAPS Pellets Coated With 11.3 ug/mm$^2$ PVA

| Diameter/wt | 10 mg | 12 mg | 20 mg | 30 mg | 40 mg | 50 mg | 56 mg |
|---|---|---|---|---|---|---|---|
| 2.4 mm | 75 g | 53 g | 72 g | 66 g | — | — | — |
| 2.8 mm | 81 g | — | 77 g | 64 g | — | — | — |

TABLE II-continued

Peak Weight Gain
CuAPS Pellets Coated With 11.3 ug/mm² PVA

| Diameter/wt | 10 mg | 12 mg | 20 mg | 30 mg | 40 mg | 50 mg | 56 mg |
|---|---|---|---|---|---|---|---|
| 3.2 mm | — | — | 80 g | 78 g | 62 g | 76 g | 79 g |

Uncoated Controls - 58 g (Avg)

Peak weight gain for the test animals with the coated pellets was attained on average on the 20th day after implantation, while peak weight gain for the control group with uncoated pellets occurred on the 11th day. These data demonstrate the prolonged release and enhanced performance obtained by means of the PVA coating in accordance with the present invention. The results of the above studies further demonstrated that PVA coatings of similar thickness result in similar bioactivity for pellets of different diameters and weights. Conversely, when the pellets of different weights were coated with 2.5% by weight PVA, the rat study demonstrated decreased activity for the larger, heavier pellets which had a thicker coating than the smaller, lighter pellets. Thus, optimum performance is obtained by providing the pellets with an optimum PVA coating thickness. For the CuAPS pellets and PVA polymer of the present study, the optimum PVA coating application appears to be in the range of 5 to 15 ug/mm² surface area. This value however, may vary for different somatotropin products and with PVA polymers having a different degree of hydrolysis, molecular weight or other properties.

EXAMPLE 2

Following the procedure of Example 1, 3.2 mm/30 mg CuAPS pellets were coated with varying amounts of PVA ranging from 1.2% by weight to 2.3% by weight in order to determine the optimum level of coating for this specific pellet. The results of the rat assay indicate maximum bioactivity at 1.2-1.5% by wt PVA, corresponding to a uniform coating application of 7.4 to 9.3 ug/mm². A similar study on 2.4 mm/12 mg CuAPS pellets indicated maximum bioactivity at 1.9-3.0% by wt. PVA corresponding to a uniform coating application of 8.6 to 13.6 ug/mm².

EXAMPLE 3

Other studies on CuAPS pellets (2.4 mm/12 mg) to determine the effect of PVA solution concentration and coating thickness on bioactivity indicated the optimum coating level for PVA solutions of 2.5-10% polymer to be as indicated in Table III below. SEM micrographs revealed larger and more frequent holes in the coatings applied from the 10% solution and essentially no holes in coatings from the 2.5% solution. While not wishing to be bound by theory, it appears that bioavailability of the coated pellet is dependent on both coating thickness and integrity, and that in general, less porous coatings obtained from more dilute solutions of PVA are more effective barriers and must be applied with less thickness than more porous coatings to obtain the same result. Thus, it will be apparent that the effect of the PVA coating on the release of bioactive material from the coated substrate will depend upon the concentration of the solution from which the PVA is applied and the method of application, as well as individual characteristics of the PVA and the underlying substrate, and that optimization of the coating is best determined empirically for each specific set of circumstances.

TABLE III

Optimum PVA Coating Levels
CuAPS Pellets Coated With 2.5-10% PVA Solutions

| | Optimum Coating Level | |
|---|---|---|
| % PVA Soln | Wt. % | Wt./Area |
| 2.5 | 1.6-2.0 | 7.2-9.0 ug/mm² |
| 5.0 | 0.8-1.9 | 3.6-8.6 |
| 10.0 | 2.0-2.3 | 9.0-10.4 |

Studies on the effect of compaction conditions on the bioactivity of PVA coated CuAPS pellets indicated that a lower degree of compaction resulted in greater bioactivity for a shorter duration. Analysis of compacted pellets indicated that modifications to the molecular structure of CuAPS resulting from the forces of compaction resulted in decreased solubility with a projected slower release rate. Accordingly, the variables of the PVA coating must be correlated with the physical characteristics of the pellet and its method of preparation in order to obtain optimum pellet performance upon implantation.

EXAMPLE 4

Compacted ABS, (2.4 mm/20 mg) prepared from ala-val-bovine somatotropin produced as described in U.S. Pat. No. 4,863,736 were coated with 16K, 25K and 40K molecular weight PVA at approximately 1.5 to 3% by weight PVA addition. The PVA coated pellets were evaluated for bioactivity with the results indicated in Table IV.

TABLE IV

ABS Pellets Coated With PVA

| No. | Polymer MW | Coating Wt. % | Coating Wt./Area | Result |
|---|---|---|---|---|
| 1 | 40,000 | 1.7 | 9.2 ug/mm² | 0 |
| 2 | 40,000 | 3.3 | 17.8 | — — |
| 3 | 25,000 | 1.7 | 9.2 | — |
| 4 | 25,000 | 3.3 | 17.8 | — |
| 5 | 16,000 | 1.4 | 7.6 | + |
| 6 | 16,000 | 2.7 | 14.6 | — |
| 7 | uncoated control | | | 0 |

In the rat assay, the pellet coated with 1.4% of 16K MW PVA (No. 5) was generally superior to the uncoated control, while the pellet coated with 3.3% of 40K MW PVA (No.2) was significantly less bioactive than the control. The remaining pellets were either substantially equivalent to the control (0) or slightly less bioactive (—). In the above study, no effort was made to optimize the coating for the specific lot of pellets used in the test. The results of the study are therefore limited to an assessment of relative bioactivity under the test conditions and demonstrate the effectiveness of 16K MW PVA as a coating material at 1.4% add-on, corresponding to a uniform average coating of 7.6 ug/mm².

EXAMPLE 5

Compacted pellets of ABS (2.4 mm/20 mg) were coated with increasing amounts of a 10% solution of Elvanol PVA (Mn 50,000) and evaluated for bioactivity in the rat assay with the results indicated in Table V below:

TABLE V

Peak Weight Gain
ABS Pellets Coated With PVA

| PVA Coating | | Peak Weight | Day of |
|---|---|---|---|
| Wt. % | Wt./Area | Gain, g | Peak Wt. |
| 1.2 | 6.5 ug/mm$^2$ | 80 | 13 |
| 1.4 | 7.6 | 80 | 13 |
| 2.0 | 10.8 | 84 | 14 |
| 2.2 | 11.9 | 97 | 15 |
| 2.4 | 13.0 | 92 | 15 |
| 0 | — Control | 63 | 10 |

The above data indicate all coating levels to be effective in enhancing bioactivity of the ABS pellets with optimum result obtained at about 2.2 wt. % PVA corresponding to a uniform coating application of 11.9 ug/mm$^2$. The data also illustrate the prolonged release effect resulting from the PVA coating.

EXAMPLE 6

Compacted pellets of ABS and PST were spray coated with 10% solutions of Aldrich PVA (Aldrich Chemical Company, Inc., Milwaukee, Wis.) having nominal M.W. values of 10K, 35K, 115K and 126K in a laboratory fluid bed apparatus. A spraying volume of approximately 25 ml polymer solution was applied to batches of 100 pellets over a period of 3.5 minutes. Weight and thickness of the PVA coating were not determined. Bioactivity of the coated pellets was determined in a rat assay with the results shown in Table VI.

TABLE VI

Peak Weight Gain
PVA Coated ABS and PST Pellets

| | ABS | | PST | |
|---|---|---|---|---|
| PVA M.W. | Peak Wt. Gain, g. | Day of Peak Wt. | Peak Wt. Gain. g. | Day of Peak Wt. |
| 10,000* | 62.1 | 10 | 56.8 | 10 |
| 35,000 | 81.0 | 16 | 78.5 | 20 |
| 115,000 | 68.4 | 13 | 79.9 | 21 |
| 126,000 | 73.6 | 11 | 74.8 | 20 |
| Control | 67.2 | 10 | 60.9 | 12 |

*88% degree of hydrolysis.

The above data demonstrate that, with the exception of the 10K MW polymer, all PVA coatings were effective to prolong and enhance the biological effect of the somatotropin pellets. The lower MW of the 10K polymer, combined with the low degree of hydrolysis, apparently resulted in this polymer being quickly dissolved upon implantation of the pellet with no significant effect on bioactivity. The other polymers used in the study were fully hydrolyzed.

The preceding Examples illustrate the application of the present invention to compacted pellets of bovine and porcine somatotropin. The somatotropin pellets coated in accordance with the present invention may contain lubricants, binders and other inactive or physiologically active materials, all of which are well known to those skilled in the art. In addition, the method of the present invention whereby a coating of polyvinyl alcohol is applied to a solid dosage form of a bioactive material as a means of controlling the release of the active material upon parenteral administration to an animal is applicable to bioactive materials other than growth hormones. Moreover, gelling agents, plasticizers, cross-linkers, biocidal agents, and various other compatible polymers may be added to the polyvinyl alcohol to modify the properties thereof and/or alter the rate of release of bioactive material from the encapsulated core. These and other variations of the present invention will be apparent to those skilled in the art and are included within the scope of the present invention.

We claim:

1. A coated veterinary implant of a growth hormone having extended release delivery characteristics upon parenteral administration to an animal, said implant comprising a solid core of said growth hormone in an amount sufficient to provide an effective dose for the desired biological response over an extended period of delivery, and a release inhibiting coating of polyvinyl alcohol continuously enveloping said core, said polyvinyl alcohol having a molecular weight of at least about 10,000, a degree of hydrolysis of at least about 95%, and being present in an amount of from about 0.5 to 5 percent by weight of said implant.

2. The implant of claim 1 wherein said coating of polyvinyl alcohol is present in an amount of from about 3 to 25 ug/mm$^2$.

3. The implant of claim 1 wherein said coating of polyvinyl alcohol is substantially uniform over the surface of said core of growth hormone.

4. The implant of claim 1 wherein said growth hormone is bovine or porcine somatotropin.

5. The implant of claim 4 wherein said somatotropin is associated with a metal ion.

6. The implant of claim 5 wherein said somatotropin is porcine and said metal ion is copper.

7. The implant of claim 5 wherein said somatotropin is bovine and said metal ion is zinc.

8. The implant of claim 1 in the form of a pellet having a cylindrical, oval or spherical shape.

9. The implant of claim 1 wherein said polyvinyl alcohol has a molecular weight of from about 20,000 to 100,000.

10. The implant of claim 9 wherein said polyvinyl alcohol has a degree of hydrolysis of at least about 98%.

* * * * *